United States Patent [19]

Mito et al.

[11] Patent Number: 5,611,785
[45] Date of Patent: Mar. 18, 1997

[54] LUER NEEDLE UNIT AND INJECTOR

[75] Inventors: Yutaka Mito; Hitoshi Katayama, both of Sanda; Hisao Tobiki, Chiyoda, all of Japan

[73] Assignee: Nihon Medi-Physics Co., Ltd., Nishinomiya, Japan

[21] Appl. No.: 576,162

[22] Filed: Dec. 21, 1995

Related U.S. Application Data

[63] Continuation of Ser. No. 285,135, Aug. 3, 1994, abandoned.

[30] Foreign Application Priority Data

Aug. 6, 1993 [JP] Japan .................................. 5-195944

[51] Int. Cl.⁶ .............................. A61M 5/00; A61M 5/31
[52] U.S. Cl. ........................ 604/239; 604/240; 604/905
[58] Field of Search .................................. 604/239, 283, 604/80, 81, 240–243, 273, 198, 264, 905, 411, 191; 285/290, 921

[56] References Cited

U.S. PATENT DOCUMENTS

| | | |
|---|---|---|
| 2,870,765 | 1/1959 | Henderson . |
| 3,247,850 | 4/1966 | Gettig et al. .............................. 604/240 |
| 3,967,621 | 7/1976 | Schwarz ............................... 604/206 X |
| 4,051,850 | 10/1977 | Tischlinger . |
| 4,084,588 | 4/1978 | Koenig . |
| 4,240,425 | 12/1980 | Akhavi ............................... 604/243 X |
| 4,424,057 | 1/1984 | House ....................................... 604/88 |
| 4,720,285 | 1/1988 | Pickhard .................................. 604/192 |
| 4,747,839 | 5/1988 | Tarello et al. ........................... 604/240 |
| 4,781,701 | 11/1988 | Geprägs .................................... 604/240 |
| 4,927,417 | 5/1990 | Moncada et al. ......................... 604/198 |
| 5,066,286 | 11/1991 | Ryan ......................................... 604/240 |
| 5,066,287 | 11/1991 | Ryan ......................................... 604/240 |
| 5,112,327 | 5/1992 | Iinuma et al. ............................ 604/413 |
| 5,256,151 | 10/1993 | Chul ......................................... 604/195 |
| 5,261,572 | 11/1993 | Strater ....................................... 222/215 |
| 5,290,222 | 3/1994 | Feng et al. .................................. 604/86 |
| 5,389,086 | 2/1995 | Attermeier et al. ..................... 604/242 |
| 5,501,676 | 3/1996 | Niedospial et al. ..................... 604/283 |
| 5,531,711 | 7/1996 | Attermeier et al. ..................... 604/242 |

FOREIGN PATENT DOCUMENTS

| | | |
|---|---|---|
| 77304/75 | 7/1976 | Australia . |
| 0379177 | 1/1990 | European Pat. Off. . |
| 2-96149 | 7/1990 | Japan . |
| 9105581 | 5/1991 | WIPO ..................................... 604/905 |

*Primary Examiner*—Robert A. Hafer
*Assistant Examiner*—V. Alexander
*Attorney, Agent, or Firm*—Jones, Tullar & Cooper, P.C.

[57] ABSTRACT

A luer needle unit and an injector effectively prevent a user's fingers from being hurt when a disposable needle is separated from the luer needle after use, while realizing simple and positive attachment of the luer needle to a supporting cap. Guide protrusions and guide recesses are provided between the luer needle and the supporting cap to prevent the rotation thereof. Guiding projecting portions are formed in the supporting cap to guide a needle part of the luer needle in the axial direction.

8 Claims, 7 Drawing Sheets

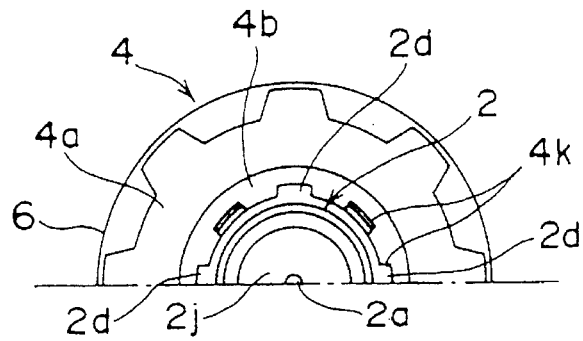
Fig. 7A
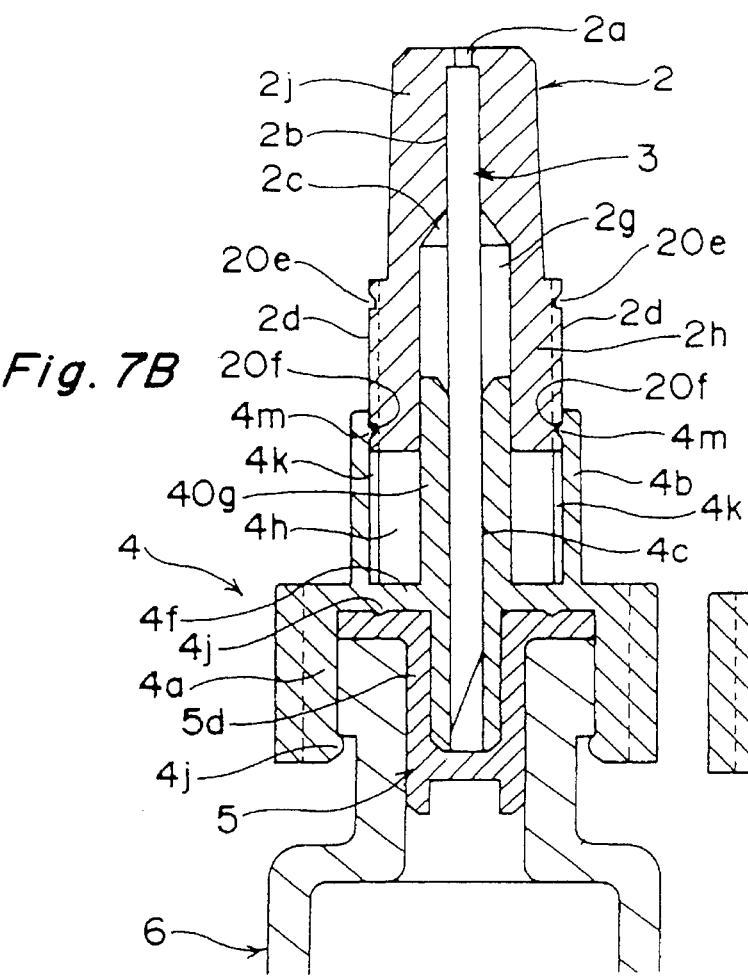
Fig. 7B
Fig. 7C
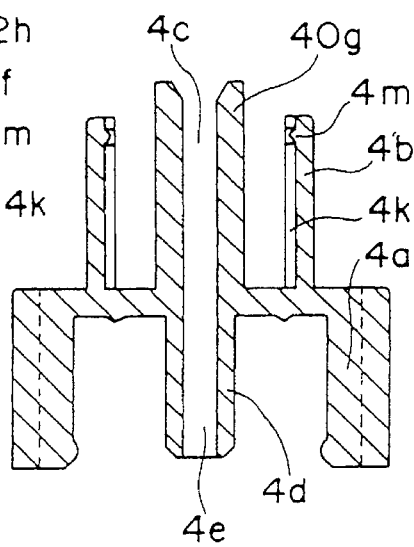
Fig. 7D

LUER NEEDLE UNIT AND INJECTOR

This is a continuation of application Ser. No. 08/285,135 filed on Aug. 3, 1994, now abandoned.

BACKGROUND OF THE INVENTION

The present invention generally relates to a luer needle unit and an injector for medical use, and more particularly to a luer needle unit used along with a prefilled syringe, that is, a syringe having pharmaceutical liquid preliminarily filled therein and which allows setting of a disposable needle thereto, and an injector using the luer needle unit.

An injector of the aforementioned type has been constructed having various structural configuration. For example, in an injector disclosed in Japanese Utility Model Laid-Open Publication No. 2-96149 (96149/1990), a luer needle is preliminarily set to a supporting cap for supporting it fitted at a mouth of a prefilled syringe. While a needle part of the luer needle is held not to penetrate a sealing cap of the syringe before the use, a disposable needle is fixed at the outside of the luer needle and pressed together with the luer needle to the syringe at the time it is used, whereby the needle part pierces the sealing cap to allow the pharmaceutical liquid in the syringe to flow out through the needle part.

In the above construction, since it is necessary to rotate and pull out disposable needle from the syringe after the use in order to dispose of the disposable needle, in some cases, the luer needle alike is rotated and inadvertently taken out concurrently with the disposable needle. The needle part of the pulled out luer needle may hurt the fingers or the like of a user. Moreover, at the setting time of the luer needle to the supporting cap after the supporting cap is fitted at the mouth of the syringe, it may undesirably take place that the needle part of the luer needle pierces the supporting cap due to the absence of a guiding member for the needle part. Therefore, it has been difficult to set the luer needle to the supporting cap.

SUMMARY OF THE INVENTION

Accordingly, an object of the present invention is to provide a luer needle unit and an injector effectively preventing a user's fingers from being hurt when a disposable needle is to be detached from a luer needle after use while allowing simple and positive mounting of the luer needle to a supporting cap.

In accomplishing this and other objects, according to one aspect of the present invention, there is provided a luer needle unit comprising:

a luer needle supporting cap to be fitted at a mouth of a syringe having pharmaceutical liquid filled therein beforehand, and a luer needle having one needle part which is selectively held in engagement with the supporting cap at a non-use position where the needle part does not pierce a syringe cap provided at the mouth of the syringe and at a use position where the needle part pierces the syringe cap and, to which a disposable needle is setable, wherein the supporting cap has a flange portion, a cylindrical guiding projecting portion extending at one side of the flange portion and having a through hole through which the needle part is penetrable, and a cylindrical portion extending at the other side of the flange portion to be fitted in the mouth of the syringe, so that a fitting portion of the luer needle is fitted outside the guiding projecting portion due to guidance of the guiding projecting portion, guide protrusions extend in an axial direction of the syringe at one of the confronting surfaces of the supporting cap and luer needle, which are engaged with guide recesses formed at the other of the confronting surfaces of the supporting cap and the luer needle in the axial direction of the syringe, thereby prohibiting relative rotation of the luer needle and the supporting cap and to guide engagement of the luer needle with the supporting cap in the axial direction of the syringe, and a distance at the two positions of the luer needle to the supporting cap is not smaller than a sum of an axial distance between a front end and a base end of a notch portion of the needle part of the luer needle and a thickness of the syringe cap.

According to another aspect of the present invention, there is provided an injector equipped with a luer needle unit comprising:

a luer needle supporting cap to be fitted at a mouth of a syringe having pharmaceutical liquid filled therein beforehand, and a luer needle having one needle part which is selectively held in engagement with the supporting cap at a non-use position where the needle part does not pierce a syringe cap provided at the mouth of the syringe and at a use position where the needle part pierces the syringe cap and, to which a disposable needle is setable, wherein the supporting cap has a flange portion, a cylindrical guiding projecting portion extending at one side of the flange portion and having a through hole through which the needle part is penetrable, and a cylindrical portion extending at the other side of the flange portion to be fitted in the mouth of the syringe, so that a fitting portion of the luer needle is fitted outside the guiding projecting portion due to guidance of the guiding projecting portion, guide protrusions extend in an axial direction of the syringe at one of the confronting surfaces of the supporting cap and luer needle, which are engaged with guide recesses formed at the other of the confronting surfaces of the supporting cap and the luer needle in the axial direction of the syringe, thereby prohibiting relative rotation of the luer needle and the supporting cap and to guide engagement of the luer needle with the supporting cap in the axial direction of the syringe, and a distance at the two positions of the luer needle to the supporting cap is not smaller than a sum of an axial distance between a front end and a base end of a notch portion of the needle part of the luer needle and a thickness of the syringe cap.

BRIEF DESCRIPTION OF THE DRAWINGS

These and other objects and features of the present invention will become clear from the following description taken in conjunction with the preferred embodiments thereof with reference to the accompanying drawings, in which:

FIGS. 7A, 7B, 7C, and 7D are a plan view of the upper half of the luer needle unit of FIG. 6 before an injector is used, a sectional view of the injector of the luer needle unit, a bottom view of the lower half of the injector, and a sectional view of a supporting cap respectively.

DETAILED DESCRIPTION OF THE PREFERRED EMBODIMENTS

Figure 1:
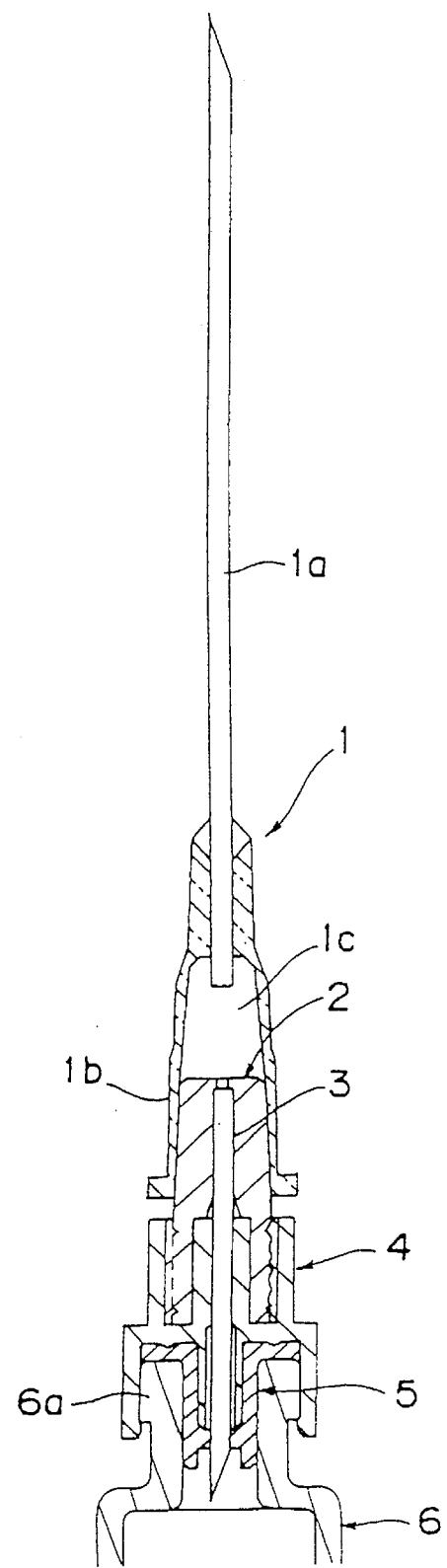
FIG. 1 is a sectional view of a part of an injector with a luer needle unit in one embodiment of the present invention.

Before the description of the present invention proceeds, it is to be noted that like parts are designated by like reference numerals throughout the accompanying drawings.

A preferred embodiment of the present invention will be described in detail with reference to FIGS. 1–7.

As shown in FIG. 1, an injector according to the embodiment has a syringe cap 5 provided at a mouth 6a of a syringe 6 in which pharmaceutical liquid is already filled. A needle part 3 of a luer needle 2 is penetrable through the syringe cap 5. A luer needle supporting cap 4 is set at the mouth 6a so that the luer needle 2 can be held in engagement with the supporting cap 4 at two positions, that is, a non-use position where a front notch portion 3a of the needle part 3 of the luer needle 2 does not pierce the syringe cap 5 and a use position where the front notch portion 3a penetrates the syringe cap 5. At the same time, a disposable needle 1 can be set to the luer needle 2. The luer needle unit is thus composed of the supporting cap 4 and the luer needle 2.

The disposable needle 1 has a needle main body 1a and a generally cylindrical fitting part 1b which supports the needle main body 1a and can be fitted into the outer periphery of the luer needle 2. The fitting part 1b is desirably formed of transparent material so that a blood vessel is confirmed at a hollow 1c between the luer needle 2 and the main body 1a.

Figure 2:
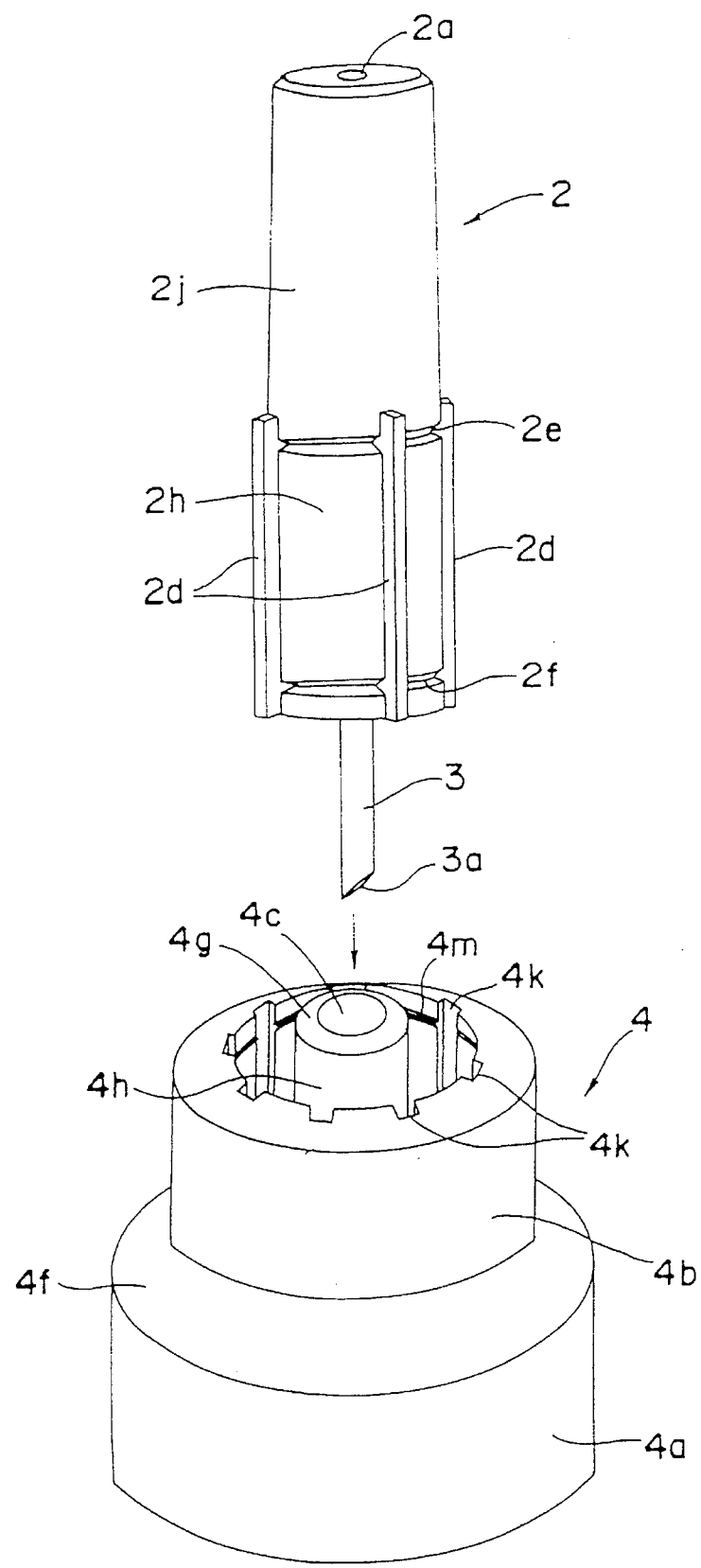
FIG. 2 is an exploded perspective view of the luer needle unit of FIG. 1.
Figure 3A:
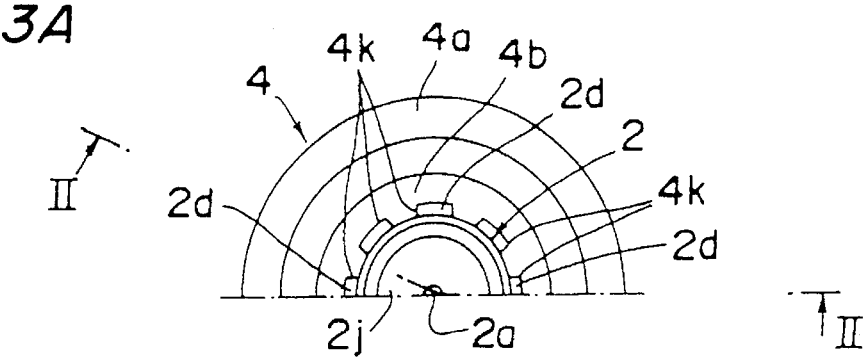
FIGS. 3A, 3B and 3C are a plane view of the upper half of the luer needle unit before the injector is used, a sectional view of the injector taken along a line II—II of FIG. 3A, and a bottom view of the lower half of the injector, respectively.
Figure 3B:
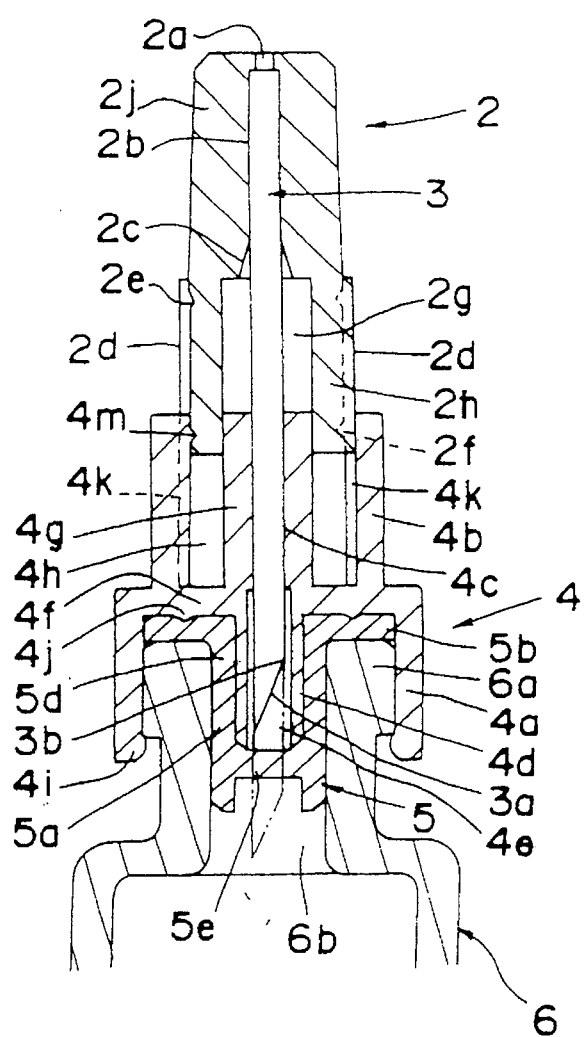
Figure 3C:
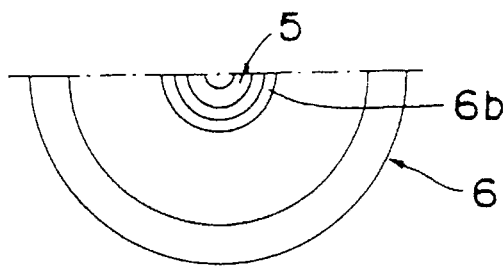

As shown in FIGS. 1–3, the mouth 6a of the syringe 6 is so constructed that an inner surface of a through hole 6b and an outer end face of the mouth 6a are kept in tight contact with the syringe cap 5 made of elastic material such as rubber or the like. Pharmaceutical liquid is sealed in the syringe 6. The syringe cap 5 has a flange portion 5b able to be tightly held in touch with the outer end face of the mouth 6a and, a cylindrical leg portion 5a extended from the flange portion 5b and tightly fitted in the through hole 6b of the mouth 6a. A front end of the needle part 3 of the luer needle 2 is accommodated in an inner fitting recess 5d of the leg portion 5a as will be described later. The needle part 3 pierces a bottom 5e of the inner fitting recess 5d when the injector is used.

The supporting cap 4 is generally an integral body of two, large and small cylindrical portions 4a, 4b, respectively via a flange portion 4f. More specifically referring to FIGS. 1–3, the lower cylindrical portion 4a of a larger diameter projecting downward from the flange portion 4f has an engaging projection 4i at the inner peripheral face at the lower end thereof. The supporting cap 4 is accordingly securely fitted at the outer peripheral part of the mouth 6a of the syringe 6, and prevented from slipping off from the mouth 6a. An annular protrusion 4j like a wedge in section is formed at the lower inner face of the flange portion 4f. When the engaging projection 4i is fitted at the syringe mouth 6a, the annular protrusion 4j is pressed in the upper surface of the syringe cap 5 thereby to enhance the contact between the syringe mouth 6a and the syringe cap 5. A cylindrical guide portion 4d of a small diameter extends downwardly from the central part of the lower face of the flange portion 4f inside the lower cylindrical portion 4a, which is fitted into the inner recess 5d of the syringe cap 5 to smoothly guide the needle part 3 of the luer needle 2 in the axial direction along a needle through hole 4e thereinside. The provision of the cylindrical guide portion 4d is not necessarily required if it is not necessary to guide the needle part 3 in the axial direction. The upper cylindrical portion 4b of a smaller diameter than that of the lower cylindrical portion 4a projects at the upper side of the flange portion 4f which is an upper end face of the lower cylindrical portion 4a. Further, a guiding projecting portion 4g projects upward from the central part at the upper face of the flange portion 4f so as to guide the luer needle 2 in the axial direction when the luer needle 2 is fitted into the supporting cap 4, as will be described later. A through hole 4c formed at the central part of the guiding projecting portion 4g serves to guide the luer needle part 3 smoothly. As indicated in FIG. 3A, there are also provided eight rectangular, curved guiding recesses 4k, in the inner peripheral face of the upper cylindrical portion 4b. The guiding recesses 4k are separated equal distances in the circumferential direction and elongated in the axial direction of the upper cylindrical portion 4b. An annular engaging protrusion 4m in the shape of a projecting wedge in section extends at the inner peripheral face of the upper end of the upper cylindrical portion 4b in the circumferential direction orthogonal to the axial direction of the syringe 6.

The luer needle 2 has a through hole 2a at the upper face of a main body 2j. The through hole 2a is smaller in diameter than the needle part 3. Moreover, the luer needle 2 has a fitting recess 2b continuous with the through hole 2a. As the needle part 3 is fitted and bonded into the fitting recess 2b, the luer needle 2 is fixed to be unable to move in the axial direction. Since the diameter of the through hole 2a is made smaller than that of the needle part 3, the needle part 3 is surely prevented from popping up from the luer needle 2, namely, towards the disposable needle when the luer needle 2 is pressed towards the supporting cap 4 from the non-use position to the use position. A reference 2c in FIG. 3B indicates a conical surface to smoothly guide the needle part 3 from below the luer needle 2 into the fitting recess 2b. A cylindrical fitting portion 2h extends in the axial direction of the syringe 6 at the lower side of the main body 2j. The fitting portion 2h is set in a luer needle-insertion recess 4h formed between the cylindrical guiding projecting portion 4g and the upper cylindrical portion 4b of the supporting cap 4, and the guiding projecting portion 4g of the supporting cap 4 is fitted in a recess 2g inside the cylindrical fitting portion 2h. In other words, the fitting portion 2h is guided by the guiding projecting portion 4g at the inside thereof, and also by the upper cylindrical portion 4b at the outside thereof. Therefore, the luer needle 2 is more smoothly inserted into the supporting cap 4. The needle part 3 of the luer needle 2 is smoothly guided in the axial direction owing to the through hole 4c in the guiding projecting portion 4g and the through hole 4e of the cylindrical guide portion 4d communicating with the through hole 4c. The cylindrical fitting portion 2h has four guide protrusions 2d spaced an equal distance in the circumferential direction and elongated in the axial direction at the outer face thereof. Therefore, when the guide protrusions 2d are engaged with four of the eight guide recesses 4k of the supporting cap 4, the luer needle 2 is smoothly guided in the axial direction to be fitted to the supporting cap 4. At the same time, the relative rotation of the luer needle 2 to the supporting cap 4 is prevented when the luer needle 2 is set to the supporting cap 4 or when the disposable needle 1 is removed. Furthermore, at the lower and upper ends of the outer peripheral face of the cylindrical fitting portion 2h of the luer needle 2, engaging recesses 2f, 2e are formed in the shape of a recessed wedge in section and are elongated in the orthogonal direction to the axial direction of the syringe 6. At the non-use position where the front end of the needle part 3 of the luer needle 2 does not pass through the syringe cap 5 before use, the engaging protrusion 4m of the supporting cap 4 is engaged with the engaging recess 2f at the lower end of the luer needle 2. On the other hand, at the use position with the front notch portion 3a of the needle part 3 penetrating the syringe cap 5, the engaging protrusion 4m is engaged with the upper engaging recess 2e of the luer needle 2.

Figure 4A:
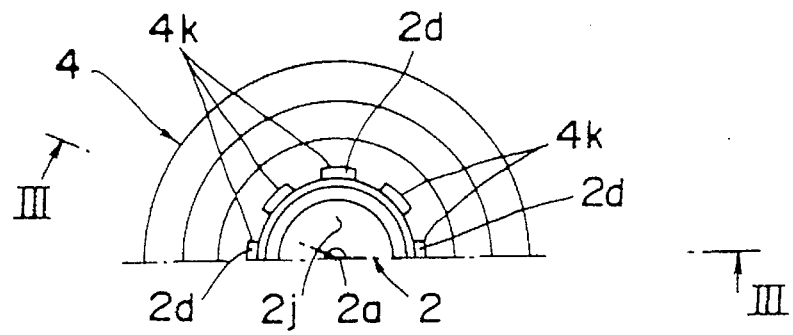
FIGS. 4A, 4B and 4C are a plan view of the upper half of the luer needle unit when the injector is used, a sectional view of the injector taken along a line III—III of FIG. 3A, and a bottom view of the lower half of the injector, respectively.
Figure 4B:
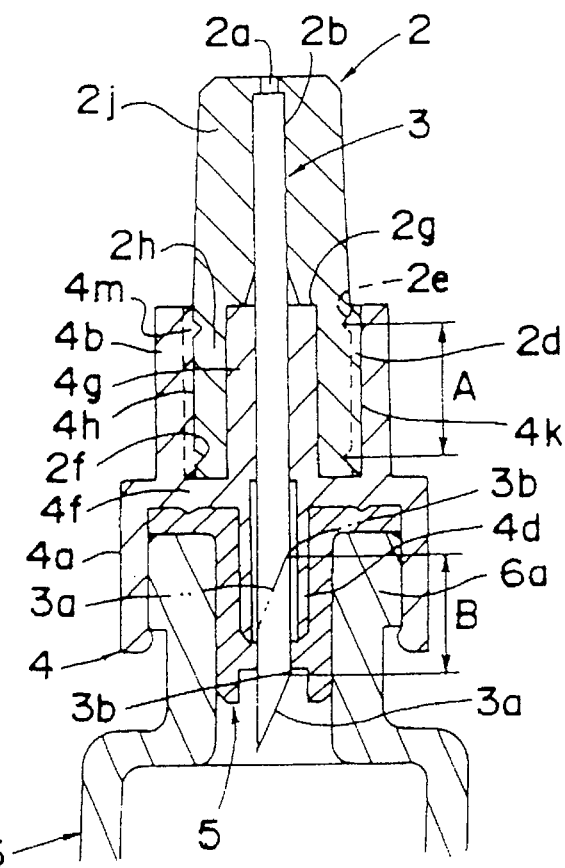
Figure 5:
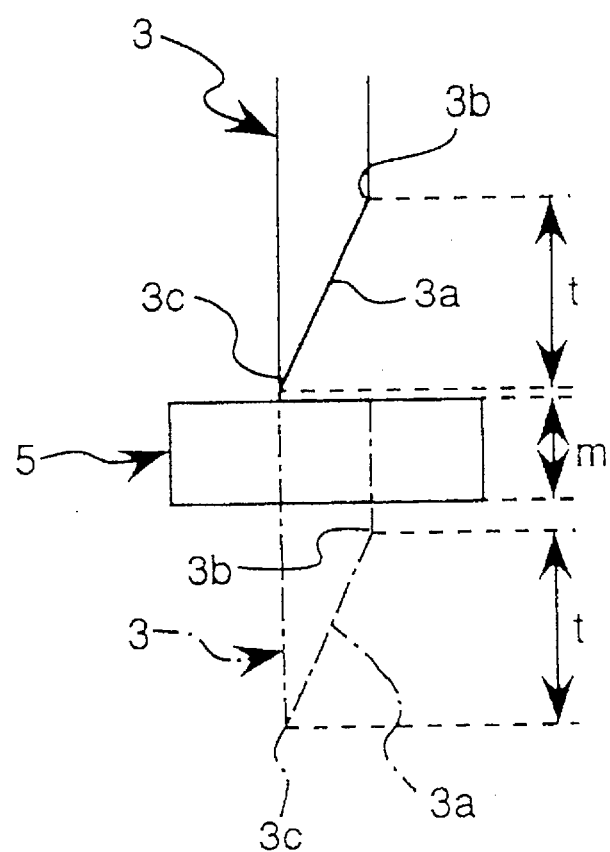
FIG. 5 is an enlarged view of a front end of a needle.

The distance A shown in FIG. 4B between the two positions, i.e., non-use position and use position of the luer needle 2 to the supporting cap 4 is not smaller than the sum of a distance t in the axial direction between a front end 3c and a base end 3b of the notch portion 3a of the needle part 3 and a thickness m of the syringe cap 5, as shown in FIG. 5. The distance A is set so that, at the non-use position before the notch portion 3a pierces the syringe cap 5, the front end 3c is retained not to penetrate the syringe cap 5 at all, whereas after piercing, the base end 3b is brought to the state fully penetrating the syringe cap 5. By setting the distance A as above, the pharmaceutical liquid in the syringe 6 is positively introduced into the needle part 3 when the luer needle 2 is moved from the non-use position to the use position in the axial direction to the supporting cap 4, because the state where the notch portion 3a of the needle part 3 does not penetrate the syringe cap 5 is changed into the state where the notch portion 3a of the needle part 3 perfectly penetrates the syringe cap 5, i.e., even the base end 3b of the needle part 3 penetrates the syringe cap 5.

In the construction described hereinabove, as shown in FIG. 3, the luer needle 2 and the supporting cap 4 are protected by a protecting cover or the like from outside before they are used in the state where the supporting cap 4 is fitted at the mouth 6a of the syringe 6 held in tight contact with the syringe cap 5 and the engaging protrusion 4m of the supporting cap 4 is engaged with the engaging recess 2f at the lower side of the luer needle 2, that is, the luer needle 2 is at the non-use position. Then, when the injector is to be used, a plunger (not shown) is inserted to a gasket (not shown) in the syringe 6 and the disposable needle 1 is fitted outside the luer needle 2. When the luer needle 2 together with the disposable needle 1 is pressed to the supporting cap 4, the lower engaging recess 2f of the luer needle 2 is separated from the engaging protrusion 4m of the supporting cap 4, so that the luer needle 2 is furthermore pressed into the supporting cap 4. As a consequence, the upper engaging recess 2e of the luer needle 2 is engaged with the engaging protrusion 4m of the supporting cap 4, whereby the luer needle 2 is set at the use position. In this state, the front notch portion 3a of the needle part 3 of the luer needle 2 penetrates the syringe cap 5, allowing the pharmaceutical liquid in the syringe 6 to flow outside through the needle part 3. The injector is thus completely assembled. After use of the injector, in order to dispose of the disposable needle 1, the disposable needle 1 is rotated about the axis of the syringe 6 with respect to the luer needle 2 prevented from rotating by the supporting cap 4 and pulled out in the axial direction of the syringe 6 from the luer needle 2. Only the disposable needle 1 can be surely separated easily from the luer needle 2 in the manner discussed above.

In the foregoing embodiment, when the luer needle 2 is to be inserted into and fitted to the supporting cap 4, the inner-side guiding projecting portion 4g and the outer-side upper cylindrical portion 4b of the supporting cap 4 guide the fitting portion 2h of the luer needle 2 smoothly in the axial direction, and moreover, the needle part 3 of the luer needle 2 is smoothly guided along the through hole 4c of the guiding projecting portion 4g. Therefore, the luer needle 2 can be smoothly and surely fitted to the supporting cap 4 in a stable manner while the needle part 3 of the luer needle 2 is prevented from piercing the supporting cap 4. The guide protrusions 2d of the luer needle 2 smoothly guide the luer needle 2 in the axial direction in engagement with the guide recesses 4k of the supporting cap 4. The engagement of the guide protrusions 2d with the guide recesses 4k positively prevents the relative rotation of the luer needle 2 and the supporting cap 4. As a result of this arrangement, even when the disposable needle 1 is to be detached by a user from the luer needle 2, in order to dispose of the disposable needle 1 after use of the injector, rotation of the luer needle 2 is rotated along with the disposable needle 1 is prevented as is detachment therefrom to hurt the user by the needle part 3.

Because of the provision of the engaging protrusion 4m and the engaging recesses 2e, 2f so as to engage the supporting cap 4 with the luer needle 2 at the non-use position and the use position, the luer needle 2 can be held positively to the supporting cap 4 at the two positions.

Moreover, since the distance of the above two positions of the luer needle 2 to the supporting cap 4 is so set as to be not smaller than the sum of the axial distance between the front end and the base end of the notch portion 3a of the needle part 3 of the luer needle 2 and the thickness of the syringe cap 5, when the luer needle 2 is moved with respect to the supporting cap 4 in the axial direction from the non-use position to the use position, the front notch portion 3a of the needle part 3 is changed from the state where the syringe cap 5 is not pierced to the state of completely penetrating the syringe cap 5, i.e., the state where even the base end 3b of the notch portion 3a penetrates the syringe cap 5. Accordingly, the pharmaceutical liquid in the syringe 6 can be positively introduced into the needle part 3.

The present invention is not limited to the above embodiment, and can be executed in various embodiments.

For instance, instead of the guiding protrusions 2d of the luer needle 2 and the guiding recesses 4k of the supporting cap 4 for preventing the rotation therebetween, guiding recesses can be provided on the luer needle 2 and guiding protrusions can be provided on the supporting cap 4. Although the above guiding protrusions and recesses 2d, 4k are formed between the outer peripheral face of the fitting portion 2h of the luer needle 2 and the inner peripheral face of the upper cylindrical portion 4b of the supporting cap 4 in the above embodiment, it can be so designed as to provide the protrusions and recesses between the inner peripheral face of the fitting portion 2h of the luer needle 2 and the outer peripheral face of the guiding projecting portion 4g of the supporting cap 4. The numbers of the protrusions and recesses are optional. If an odd number of protrusions and recesses are provided, the working force is dispersed in many directions, so that the shift resulting from the size error can be absorbed.

Moreover, the supporting cap 4 can have the guiding projecting portion 4g alone at the upper side of the flange portion 4f, with the upper cylindrical portion 4b omitted. In this case, the guiding protrusions and recesses, and the engaging protrusion and recesses are formed between the outer peripheral face of the guiding projecting portion 4g and the inner peripheral face of the fitting portion 2h of the luer needle 2.

Instead of disposing the engaging protrusion 4m only at the upper end of the upper cylindrical portion 4b, the protrusion can be formed also at the lower end of the upper cylindrical portion 4b. At the use position, therefore, the two engaging protrusions 4m are fitted with the corresponding engaging recesses 2f, 2e of the luer needle 2, whereby the luer needle is more positively held at the use position and prevented from slipping off from the supporting cap 4 after use. Likewise, the engaging protrusions and recesses can be formed between the outer peripheral face of the guiding projecting portion 4g of the luer needle 2 and the inner peripheral face of the cylindrical fitting portion 2h of the luer needle 2. The sectional shape of the protrusions and recesses need not be a wedge, but can be a circle or a trapezoid or any form so long as it ensures the engagement between the luer needle 2 and the supporting cap 4. The protrusions and recesses need not be formed annularly either.

In order to set up the injector, the way is not restricted to the above. Alternatively, the luer needle 2 can be mounted to the supporting cap 4 beforehand at the non-use position, thereby to constitute the luer needle unit. The luer needle unit is assembled with the syringe 6 having the syringe cap 5 tightly secured at the mouth 6a, and kept protected by a protecting cover or the like until the injector is used. Or, the syringe 6 equipped with the syringe cap 5 and the above luer needle unit are protected separately and, at the using time, the syringe 6 and the luer needle unit are assembled to each other and also the disposable needle 1 is set.

Figure 4C:
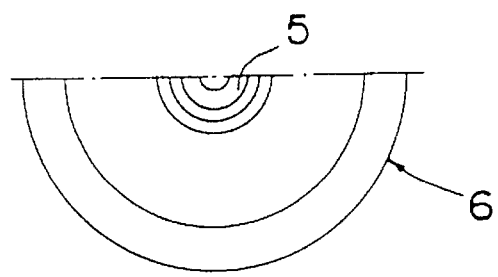
Figure 6:
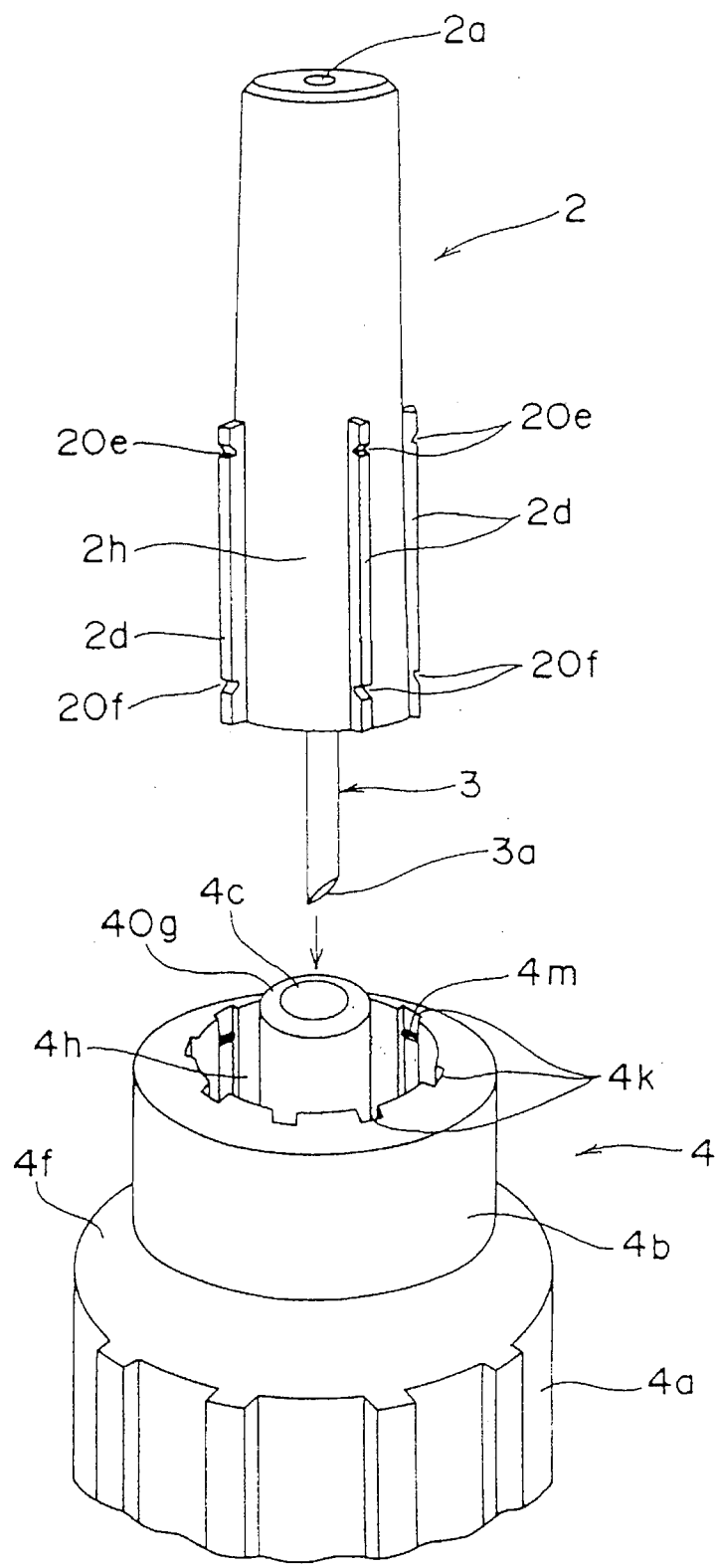
FIG. 6 is an exploded perspective view of a luer needle unit in another embodiment of the present invention.

The engaging recesses 2e, 2f are not necessarily formed in the cylindrical fitting portion 2h as illustrated in FIGS. 2–4, but can be formed on the guide protrusions 2d as are denoted by 20e and 20f in FIGS. 6, 7. In this case, the engaging protrusions 40m are formed inside the guide recesses 4k. In the arrangement as above, engaging faces can be secured at the lower ends of the upper engaging recesses 20e in a direction orthogonal to the axial direction, making it impossible to press the luer needle 2 into the supporting cap 4 from the non-use position to the use position without a certain degree of force. Similarly, the lower engaging recesses 20f can be provided with engaging faces in the orthogonal direction to the axial direction at the upper ends thereof to hinder the detachment of the luer needle 2 from the supporting cap 4 unless not smaller than a certain degree of force acts on the luer needle 2.

As shown in FIGS. 6 and 7, a guiding projecting portion 40g of the supporting cap 4 can be formed longer than the upper cylindrical portion 4b thereoutside so as to guide the needle part 3 more stably.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A luer needle unit, comprising:
   a luer needle supporting cap adapted to be fitted at a mouth of a syringe having a syringe cap and pharmaceutical liquid filled in the syringe beforehand; and
   a luer needle mounted to said supporting cap, whereby a disposable needle is settable on the luer needle, said luer needle further comprising a needle part, wherein said needle part extends away from the disposable needle and toward the syringe and is selectively held in engagement with said supporting cap at a non-use position where said needle part does not pierce the syringe cap provided at the mouth of the syringe and at a use position where said needle part pierces the syringe cap, a confronting surface, a fitting portion, and a notch portion defining a front end and a base end, wherein:
   said supporting cap has a flange portion, a cylindrical guiding projecting portion extending from one side of said flange portion and having a through hole through which said needle part penetrates, a confronting surface, and a cylindrical portion extending from the other side of said flange portion to be fitted in the mouth of the syringe, said fitting portion of said luer needle being fitted outside said guiding projecting portion and being guided by said guiding projecting portion,
   guide protrusions extending in the axial direction of the syringe at one of the confronting surfaces of said supporting cap and said luer needle, which engage with guide recesses formed at the other of the confronting surfaces of said supporting cap and said luer needle in the axial direction of the syringe, thereby prohibiting relative rotation of said luer needle and said supporting cap and providing guide engagement of said luer needle with said supporting cap in the axial direction of the syringe, and
   the two positions of said luer needle relative to said supporting cap define a distance not smaller than the sum of the axial distance between said front end and said base end of said notch portion of said needle part of said luer needle and a thickness of the syringe cap.

2. The luer needle unit as claimed in claim 1, wherein said fitting portion defines the confronting surface of said luer needle, said luer needle having an engaging protrusion extending in a direction orthogonal to the axial direction of the syringe at one of the confronting surfaces of said fitting portion and said supporting cap, while at the other of the confronting surfaces of said fitting portion and said supporting cap are formed two engaging recesses to be selectively engaged with said engaging protrusion at the non-use position and the use position.

3. The luer needle unit as claimed in claim 2, wherein said supporting cap is provided with a cylindrical outer guiding projecting portion which defines along with said guiding projecting portion a predetermined space to receive said fitting portion of said luer needle, said outer guiding projecting portion extends to one side from said flange portion thereby to guide an outer peripheral face of said fitting portion of said luer needle.

4. The luer needle unit as claimed in claim 1, wherein said supporting cap is provided with a cylindrical outer guiding projecting portion which defines along with said guiding projecting portion a predetermined space to receive said fitting portion of said luer needle, said outer guiding projecting portion extends to one side from said flange portion thereby to guide an outer peripheral face of said fitting portion of said luer needle.

5. An injector equipped with a luer needle unit, comprising:
   a luer needle supporting cap adapted to be fitted at a mouth of a syringe having a syringe cap and pharmaceutical liquid filled in the syringe beforehand; and a luer needle mounted to said supporting cap, whereby a disposable needle is settable on said luer needle, said luer needle further comprising a needle part, wherein said needle part extends away from the disposable needle and toward the syringe and is selectively held in engagement with said supporting cap at a non-use position where said needle part does not pierce the syringe cap provided at the mouth of the syringe and at a use position where said needle part pierces the syringe cap, a confronting surface, a fitting portion, and a notch portion defining a front end and a base end, wherein:

said supporting cap has a flange portion, a cylindrical guiding projecting portion extending from one side of said flange portion and having a through hole through which said needle part penetrates, a confronting surface, and a cylindrical portion extending from the other side of said flange portion to be fitted in the mouth of the syringe, said fitting portion of said luer needle being fitted outside said guiding projecting portion and being guided by said guiding projecting portion, guide protrusions extending in the axial direction of the syringe at one of the confronting surfaces of said supporting cap and said luer needle, which engage with guide recesses formed at the other of the confronting surfaces of said supporting cap and said luer needle in the axial direction of the syringe, thereby prohibiting relative rotation of said luer needle and said supporting cap and providing guide engagement of said luer needle with said supporting cap in the axial direction of the syringe, and the two positions of said luer needle relative to said supporting cap define a distance not smaller than the sum of the axial distance between said front end and said base end of said notch portion of said needle part of said luer needle and a thickness of the syringe cap.

6. The injector as claimed in claim 5, wherein said fitting portion defines the confronting surface of said luer needle, said luer needle having an engaging protrusion extending in a direction orthogonal to the axial direction of the syringe at one of the confronting surfaces of said fitting portion and said supporting cap, while at the other of the confronting surfaces of said fitting portion and said supporting cap are formed two engaging recesses to be selectively engaged with said engaging protrusion at the non-use position and the use position.

7. The injector as claimed in claim 6, wherein said supporting cap is provided with a cylindrical outer guiding projecting portion which defines along with said guiding projecting portion a predetermined space to receive said fitting portion of said luer needle, said outer guiding projecting portion extends to one side from said flange portion thereby to guide an outer peripheral face of said fitting portion of said luer needle.

8. The injector as claimed in claim 5, wherein said supporting cap is provided with a cylindrical outer guiding projecting portion which defines along with said guiding projecting portion a predetermined space to receive said fitting portion of said luer needle, said outer guiding projecting portion extends to one side from the flange portion thereby to guide an outer peripheral face of said fitting portion of said luer needle.

* * * * *